United States Patent [19]

Ogawa

[11] Patent Number: 5,254,102
[45] Date of Patent: Oct. 19, 1993

[54] APPARATUS FOR CONTROLLING THE RATE OF DRIPPING OF INTRAVENOUS FLUID

[76] Inventor: Genshiro Ogawa, 13-3 Aza-Nishikoken Oaza-Inuyama, Inuyama-shi Aichi-ken, Japan

[21] Appl. No.: 933,811

[22] Filed: Aug. 24, 1992

[30] Foreign Application Priority Data

Aug. 23, 1991 [JP] Japan .................. 3-237016
Aug. 30, 1991 [JP] Japan .................. 3-246916

[51] Int. Cl.$^5$ ........................................ A61M 5/16
[52] U.S. Cl. ........................ 604/253; 128/DIG. 13; 73/861.41; 604/65
[58] Field of Search ............ 604/65, 251, 253; 128/DIG. 13; 73/861.18, 861.23, 861.41

[56] References Cited

U.S. PATENT DOCUMENTS

| | | | |
|---|---|---|---|
| 2,807,012 | 9/1957 | Schwarz | 604/253 |
| 4,261,388 | 4/1981 | Shelton | 604/65 |
| 4,452,273 | 6/1984 | Hanzawa et al. | 604/253 |
| 4,493,710 | 1/1985 | King et al. | 604/253 |
| 4,496,351 | 1/1985 | Hillel et al. | 604/253 |
| 4,634,426 | 1/1987 | Kamen | 604/65 |
| 4,645,489 | 2/1987 | Krumme et al. | 604/65 |
| 4,652,262 | 3/1987 | Veracchi | 604/253 |
| 4,718,896 | 1/1988 | Arndt et al. | 604/253 |
| 4,909,786 | 3/1990 | Gijselhart et al. | 604/65 |
| 4,946,439 | 8/1990 | Eggers | 604/65 |

FOREIGN PATENT DOCUMENTS 2-120628  5/1990  Japan .
3-231680  10/1991  Japan .

*Primary Examiner*—Ralph Lewis
*Attorney, Agent, or Firm*—Burns, Doane, Swecker & Mathis

[57] ABSTRACT

An apparatus for controlling the rate of dripping of an intravenous fluid, comprising (i) a drip-detecting device for detecting that an intravenous fluid has dripped into a drip-feed bottle, (ii) a clock for measuring time and indicating the current time, (iii) a constricting arrangement connected to a fluid-supply pipe extending from the drip-feed bottle in a downstream direction, for constricting the supply tube, and (iv) a flow controller for controlling the amount of constriction of the supply pipe by the constricting arrangement, based on a signal from the drip-detecting device indicating detection of a drip and a time signal from the clock. The apparatus enables one to accurately control the interval of time at which an intravenous fluid drips into the drip-feed bottle and, hence, to administer the fluid to a patient at a desired rate.

12 Claims, 5 Drawing Sheets

APPARATUS FOR CONTROLLING THE RATE OF DRIPPING OF INTRAVENOUS FLUID

FIELD OF THE INVENTION

This invention relates to an apparatus for controlling the rate at which a fluid such as blood, a nutritive solution, or a Ringer's solution is administered in drips into a vein of a patient.

BACKGROUND OF THE INVENTION

The rate at which an intravenous fluid, such as blood, a nutritive solution, or a Ringer's solution, is to be administered to a patient depends upon such factors as the particular kind of operation to be performed on the patient, the seriousness of the patient's illness or injury, or the patient's pulse rate, blood pressure or heart condition. For example, 500 milliliters of intravenous fluid are usually administered in 1 to 3 hours, but are sometimes administered in 4 or 5 hours.

A conventional dripping apparatus is shown in FIG. 5. A vial 10 filled with an intravenous fluid is hung upside down on a stand (not shown). The vial 10 is stopped by a cork plug 12. A needle projecting upward from a tube 14 is inserted into the cork plug 12. The fluid flows through the needle into the tube 14. A drip-feed bottle 18 is connected to the lower end of the tube 14. The fluid that has flowed into the tube 14 drips into the drip-feed bottle 18, and remains there for a certain period of time. In the bottle 18 air bubbles are separated from the fluid. A vinyl tubing 20 is connected to the lower end of the bottle 18. An intravenous needle 32 is connected to the lower end of the vinyl tubing 20. From the bottle 18, drips of the fluid flow through the tubing 20 into the intravenous needle 32. A roller clamp 26 is connected to the vinyl tube 20. One can constrict the tubing 20 by operating the roller clamp 26. By constricting the tubing 20 or releasing it from constriction, he or she can control the rate of dripping of the fluid into the bottle 18 and, hence, the rate at which drips of the fluid are administered into a vein of the patient. However, the roller clamp 26 is operated manually and, hence, it is not easy to accurately control the rate of dripping of the fluid.

Use of a phototube has been proposed to provide a more accurate control. That is, it has been proposed that one detect the dripping of the fluid into the bottle 18 with a phototube and control the rate of dripping based on the detection thereof. This method, however, is disturbed if a shadow is accidentally thrown on the bottle 18. In addition, this method must be adjusted, through slightly, according to the kind of intravenous fluid used. Moreover, it is necessary to locate the phototube perpendicular to the direction of dripping of the fluid and, hence, it takes a relatively long time to make preparations for this method.

SUMMARY OF THE INVENTION

It is an object of the invention to provide an apparatus which enables one to accurately control the rate at which a fluid such as blood, a nutritive solution, or a Ringer's solution is administered in drips into a vein of a patient and which is free from the foregoing drawbacks of the prior art.

Another object of the invention is to provide such an apparatus having a device for detecting the dripping of an intravenous fluid into a drip-feed bottle by detecting vibrations made by the fluid dripping into the bottle.

Still another object of the invention is to provide such an apparatus having a device for detecting the dripping of an intravenous fluid into a drip-feed bottle by detecting sound waves made by the fluid dripping into the bottle.

A further object of the invention is to provide such an apparatus having a device for detecting the dripping of an intravenous fluid into a drip-feed bottle by detecting a variation in pressure caused by the fluid dripping into the bottle.

Another object of the invention is to provide such an apparatus having a drip-detecting device which can be easily connected to a supply tube extending from a drip-feed bottle in a downstream direction.

The invention is based on the inventor's finding that an intravenous fluid drips into a drip-feed bottle in substantially equal amounts by virtue of its surface tension. Then, if one determines the interval of time at which the fluid drips into the bottle, he or she can easily calculate the total amount of the fluid that has dripped into the bottle.

DETAILED DESCRIPTION OF THE PREFERRED EMBODIMENT

An apparatus which embodies the invention in one preferred form will now be described with reference to FIGS. 1 and 2.

Figure 1:
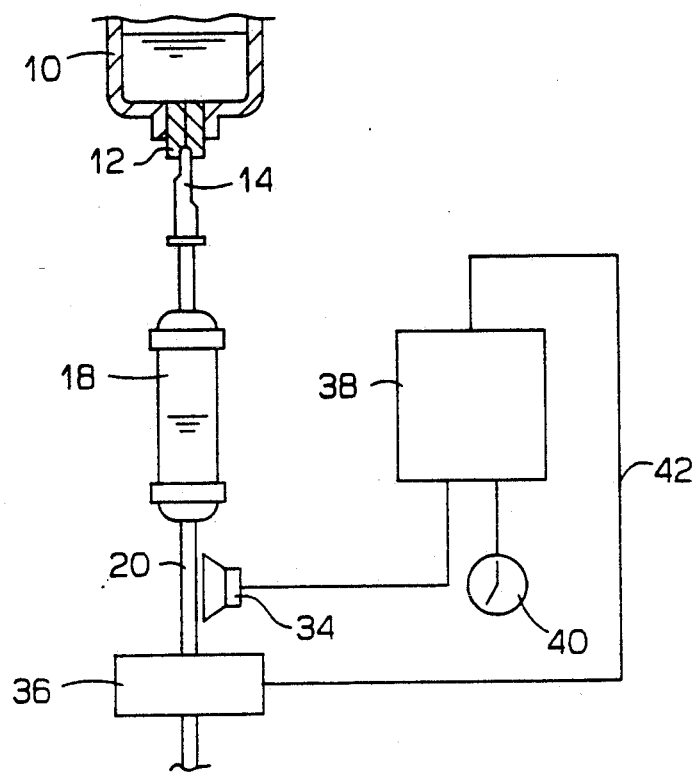
FIG. 1 shows an apparatus of the invention for controlling the rate of dripping of an intravenous fluid.

In FIG. 1 a vial 10 is hung upside down on a stand (not shown). The vial 10 is filled with a fluid, such as blood, a nutritive solution, or a Ringer's solution, to be administered in drips into a vein of a patient. The vial 10 is stopped by a cork plug 12. A needle projecting upward from a tube 14 is inserted into the cork plug 12. The fluid flows through the needle into the tube 14. A drip-feed bottle 18 is connected to the lower end of the tube 14. The fluid that has flowed into the tube 14 drips into the drip-feed bottle 18. A flexible fluid-supply tubing 20, such as a vinyl tubing, is connected to the lower end of the drip-feed bottle 18. An intravenous needle (not shown) is connected to the lower end of the tube 20. From the bottle 18, drips of the fluid flow through the tube 20 into the intravenous needle.

A microphone 34 is located below the bottle 18, and is positioned by the side of the tube 20. The microphone 34 detects the sound waves produced by a drip of the fluid falling into the drip-feed bottle 18. For example, a microphone detecting sound waves within the range of 20 cycles to 70 cycles per second may be used.

Below the microphone 34 is located a device 36 for constricting the tube 20 to adjust the rate of flow of the fluid. The constricting device 36 comprises an element (not shown) to constrict the tube 20 directly and a stepping motor (not shown) to operate the constricting element. The microphone 34 is electrically connected to flow controller 38. The sound waves detected and converted into an electrical signal by the microphone 34 are input to the flow controller 36 via an amplifier (not shown) and a frequency discriminator (not shown). A clock 40 the current time is always input to the flow controller 38. The flow controller 38 sends an electrical signal to the constricting device 36 through a transmission line 42 in order to rotate the stepping motor of the constricting device.

Figure 2:
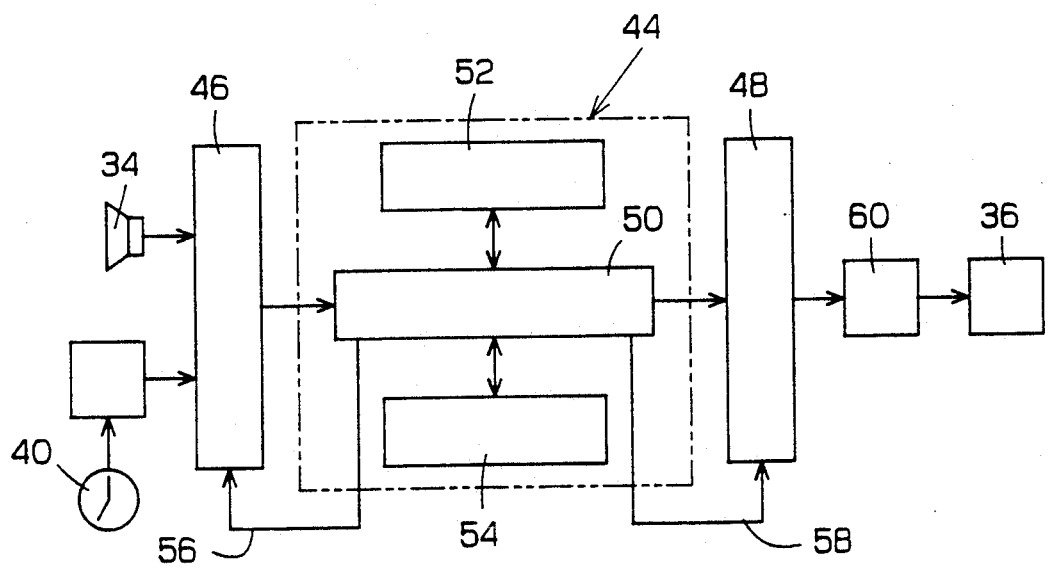
FIG. 2 shows a flow controller used for the apparatus of FIG. 1.

Referring to FIG. 2, the flow controller 38 comprises an input port 46, a microcomputer 44, and an output port 48. The electrical signal from the microphone 34, as well as a time signal from the clock 40, is input to the input port 46. The microcomputer 44 includes a CPU 50, a RAM 52, and a ROM 54. A program to control the cpu 50 is written in the ROM 54. In accordance with this program the CPU 50 receives necessary data from the input port 46 or receives or sends data from or to the RAM 52, and performs necessary arithmetic operations. The CPU 50 processes data as required, and outputs it to the output port 48. The output port 48 includes a latching circuit which receives an output port signal sent from the CPU 50 through a transmission line 58, and stores the data temporarily and outputs it to a digital-to-analog converter 60. The converter 60 converts the data from the output port 48 into an analog signal. The analog signal is output into the constricting device 36 to control the stepping motor thereof.

Figure 3:
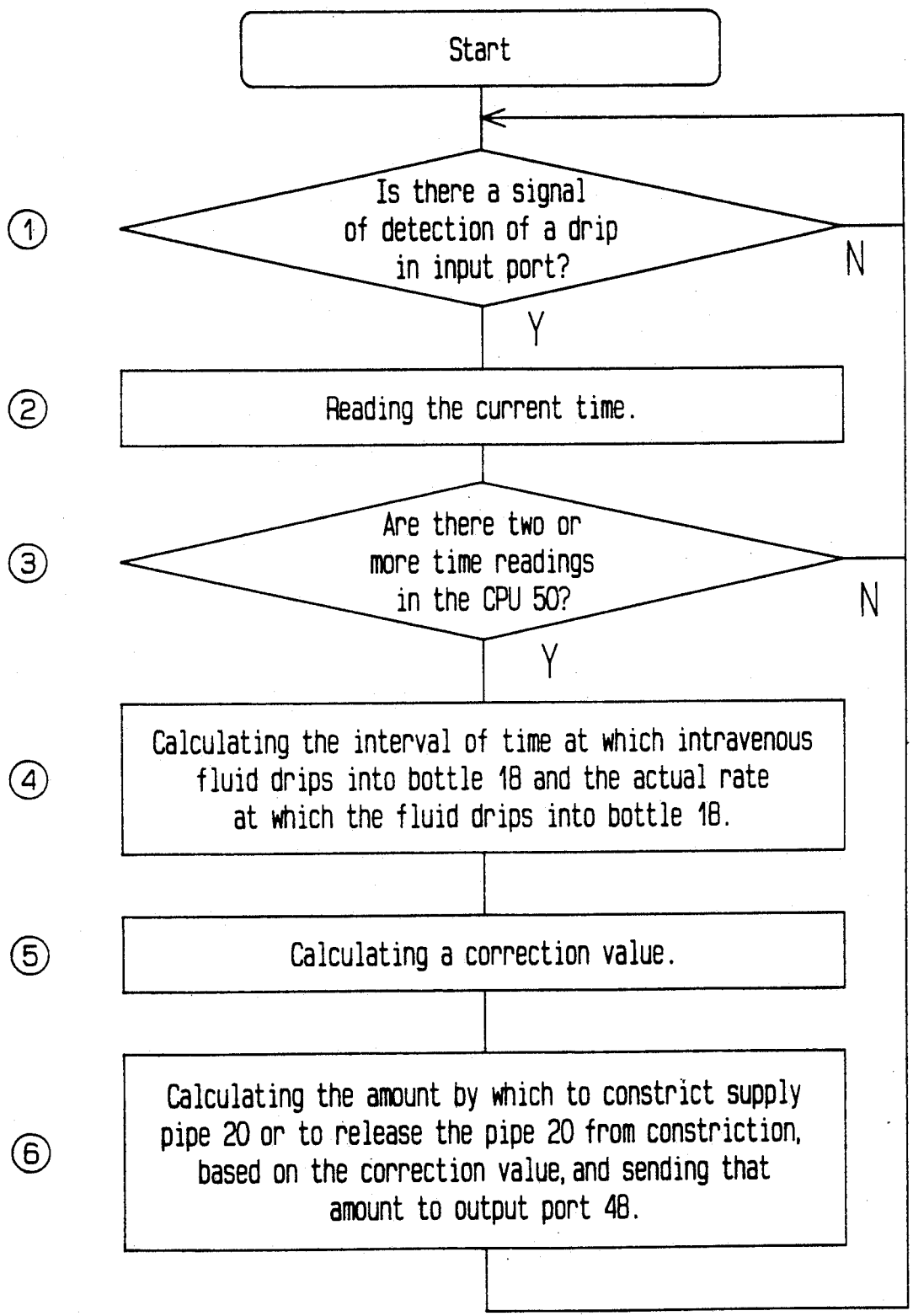
FIG. 3 is a flow chart of a computer program that may be used for the flow controller of FIG. 2.

The program written in the ROM 54 is shown in FIG. 3. When the program starts, step 1 is performed to cause the CPU 50 to send a port-specifying signal to the input port 46 through a transmission line 56 and check to see if there is a signal of detection of a drip (i.e., an electrical signal output from the microphone 34) in the input port 46. If there is one, it is input to the CPU 50. If not, program execution goes back to START. In step 2 the CPU 50 sends a port signal to the input port 26, and reads the time input to the input port 46 from the clock 40. In step 3 it is determined whether there are a total of two or more time readings, including that taken immediately before this, in the CPU 50. If not (it means that the drip detected in step 1 is the first drip), execution goes back to START. If yes, step 4 is performed. In step 4 the CPU 50 subtracts the preceding time (i.e., the time read in step 2 during the preceding execution of the program) from the current time read in step 2 (i.e., the most recent time reading) to determine the internal of time at which the intravenous fluid has dripped from the tube 14 into the drip-feed bottle 18. Also in step 4, based on data stored in the RAM 52, the CPU 50 calculates the actual rate at which the intravenous fluid drips from the tube 14 into the drip-feed bottle 18. In step 5, from the actual rate obtained in step 4 and a predetermined rate stored in the computer 44 in advance, a correction value is calculated. In step 6, based on the correction value obtained in step 5, the amount by which to constrict the supply tube 20 or to release the supply tube 20 from constriction is calculated. Also in step 6, a signal indicative of that amount is sent to the output port 48, and is output thence to the D/A converter 60 and converted into an analog signal thereby. The analog signal is output to the stepping motor of the constricting device 36. When step 6 has been completed, program execution goes back to START.

In accordance with the invention, the amount of an intravenous fluid to be administered to a patient may be programmed in advance. If such an amount has been programmed in advance, the program of FIG. 3 has the following additional steps. Between steps 2 and 3 the total amount of the intravenous fluid that has dripped into the bottle 18 is calculated, and after step 6 that total amount is compared with the programmed amount. Then, if the actual total amount is smaller than the programmed amount, execution goes back to step 1. When the programmed amount is reached, a signal is output to the constricting device 36 to cause the constricting device 36 to constrict the supply tube 20 such that the flow of intravenous fluid is stopped. Thereupon the program is completed.

In addition, in accordance with the invention, the period of time for which an intravenous fluid is to be administered to a patient may be programmed in advance. If such a period of time has been programmed in advance, the program of FIG. 3 has the following additional steps. Measurement of time that elapsed is started when the first signal of detection of a drip is detected by the CPU 50 (in step 2). After step 6, the time that has actually elapsed is compared with the programmed time. Then, if the actual time that has elapsed is shorter than the programmed period of time, execution goes back to step 1. When the programmed period of time is reached, a signal is output to the constricting device 36 to cause the constricting device 36 to constrict the supply tube 20 such that the flow of intravenous fluid is stopped. Thereupon the program is completed.

Figure 4:
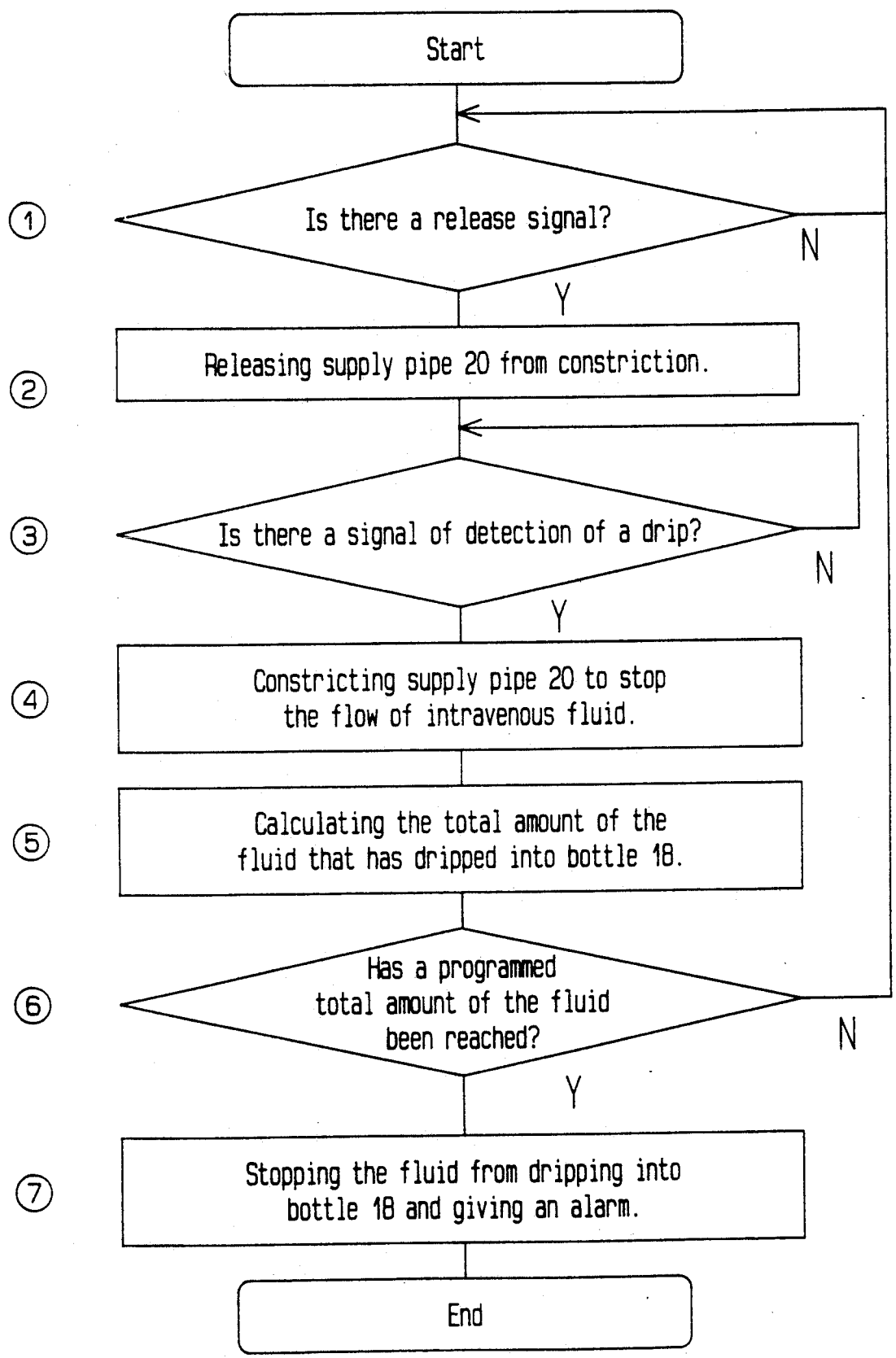
FIG. 4 is a flow chart of another computer program that may be used for the flow controller of FIG. 2.
Figure 5:
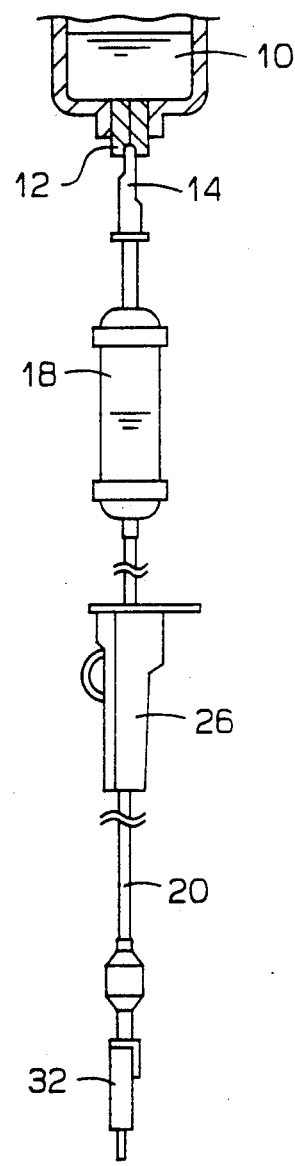
FIG. 5 shows prior art.

FIG. 4 shows a program for causing an intravenous fluid to drip at predetermined regular intervals of time. When this program is started, step 1 is performed to determine whether there is a "release signal", or a signal to rotate the stepping motor of the constricting device 36 such that the supply tube 20 is released from constriction. If not, execution goes back to START. If there is one, step 2 is performed to rotate the stepping motor for a predetermined angle such that the supply tube 20 is released from constriction. In step 3 the CPUP 50 checks to see if there is a signal of detection of a drip (of the intravenous fluid) in the input port 46. If not, execution goes back to step 2. If there is one, it is input to the CPU 50. Then, in step 4 the stepping motor is so rotated as to constrict the supply tube 20 such that the flow of intravenous fluid is stopped (by the constricting device 36). In step 5 the total amount of intravenous fluid that has dripped from the tube 14 into the bottle 18 is calculated. In step 6 it is determined whether a programmed total amount of intravenous fluid has been reached. If not, execution goes back to START. If yes, step 7 is performed to stop the fluid from dripping into the bottle 18 and give an alarm. Thereupon the program is completed.

Figure 6:
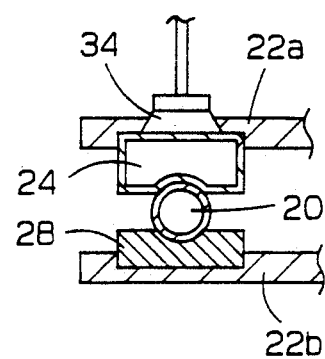
FIG. 6 shows a drip-detecting device that may be used for the apparatus of FIG. 1.

If desired, a drip-detecting device of FIG. 6 may be used for the construction of FIG. 1. The drip-detecting device of FIG. 6 includes a pair of opposed clipping elements 22a and 22b located with the supply tube 20 between. The two clipping elements are biased toward each other by means of a spring (not shown). An air bag 24 is connected to the inside of one clipping element 22a, while a cushioning element 28 is connected to the inside of the other clipping element 22b. Both the air bag 24 and the cushioning element 28 are of elastic material. A microphone 34 is located in an opening of the clipping element 22a and is connected to the outside of the air bag 24. Since the two clipping elements are biased toward each other, the air bag 24 attaches very closely to the supply tube 20. Thus, if such a drip-detecting device is used, the sound waves, or vibration, produced by the intravenous fluid dripping into the bottle 18 is transmitted, without fail, to the microphone 34 through the air bag 24. In addition, it will be appreciated that such a drip-detecting device can be very easily connected to or removed from the supply tube 20.

What is claimed is:

1. An apparatus for controlling the rate of dripping of an intravenous fluid into a drip-feed bottle that has a fluid-supply tube extending therefrom, comprising
   (a) drip-detecting means positionable on the fluid-supply tube below the drip-feed bottle for detecting the dripping of an intravenous fluid into a drip-feed bottle, said drip-detecting means comprising a pair of clipping elements positionable with the supply tube located therebetween and biased toward each other by a spring, an air bag connected to an inside of one of the clipping elements for being pressed against the supply tube, and means connected to the air bag for detecting vibrations resulting from intravenous fluid dripping into the drip-feed bottle;
   (b) a clock for measuring time and indicating the current time;
   (c) constricting means positionable on the fluid-supply tube at a position downstream of the drip-feed bottle for constricting the supply tube; and
   (d) a flow controller for controlling constriction of the supply tube by the constricting means based on a signal from the drip-detecting means indicating detection of a drip and a time signal from the clock.

2. Apparatus in accordance with claim 1, wherein the flow controller includes (i) means for determining an interval of time at which the intravenous fluid has dripped into the drip-feed bottle based on signals from the drip-detecting means indicating detection of drips, (ii) means for calculating an actual rate of dripping of the intravenous fluid into the drip-feed bottle based on said interval of time, for comparing said actual rate and a programmed ripping rate and for calculating a correction value by which to adjust said interval of time, and (iii) means for calculating an amount by which the supply tube is to be constricted based on said correction value, and for outputting to the constricting means a signal to constrict the supply tube by said amount.

3. Apparatus in accordance with claim 2, wherein the flow controller further includes (a) means for calculating a total amount of intravenous fluid that has dripped into the drip-feed bottle based on the signals from the drip-detecting means indicating detection of drips, and (b) means for outputting to the constricting means a stop signal to cause the constricting means to constrict the supply tube so that the dripping of intravenous fluid can be stopped when a programmed total amount of intravenous fluid to be administered to a patient has been reached.

4. Apparatus in accordance with claim 3, wherein the flow controller further includes means for outputting an alarm after said stop signal has been output.

5. Apparatus in accordance with claim 2, wherein the flow controller further includes (a) means for calculating a total period of time for which intravenous fluid has dripped based on signals from the drip-detecting means indicating detection of drips, and (b) means for outputting to the constricting means a stop signal for causing the constricting means to constrict the supply tube such that the dripping of intravenous fluid can be stopped when a programmed total period of time has been reached.

6. Apparatus in accordance with claim 5, wherein the flow controller further includes means for outputting an alarm after said stop signal has been output.

7. Apparatus in accordance with claim 1, wherein the flow controller includes (a) means for outputting to the constricting means a signal to rotate a stepping motor of the constricting means for a predetermined angle so that the supply tube can be released from constriction by a predetermined amount and (b) means for outputting to the constricting means a signal to rotate the stepping motor of the constricting means so that the supply tube can be constricted based on signals from the drip-detecting means indicating detection of drips.

8. Apparatus in accordance with claim 1, wherein the means for detecting vibrations comprises a microphone for detecting sound waves produced by intravenous fluid dripping into the bottle.

9. Apparatus in accordance with claim 8, including a cushioning element connected to an inside of the other clipping element.

10. Apparatus in accordance with claim 1, including a cushioning element connected to an inside of the other clipping element.

11. A drip-detecting device for detecting intravenous fluid dripping into a drip-feed bottle that has a supply tube extending downwardly therefrom, comprising a pair of clipping elements positionable below a drip-feed bottle and on a supply tube so that the supply tube is positioned between the clipping elements, said clipping elements being biased toward each other by a spring, an air bag connected to an inside of one of the clipping elements for being pressed against the supply tube, and means connected to the air bag for detecting vibrations resulting from intravenous fluid dripping into the drip-feed bottle.

12. A drip detecting-device according to claim 11, including a cushioning element connected to an inside surface of the other clipping element.

* * * * *